United States Patent [19]

Sernyk et al.

[11] Patent Number: 5,965,755
[45] Date of Patent: Oct. 12, 1999

[54] **OIL PRODUCED FROM THE *BRASSICA NAPUS***

[75] Inventors: John Lawrence Sernyk; Juan Enrique Romero Lanuza, both of Madison, Wis.

[73] Assignee: Agrigenetics, Inc., San Diego, Calif.

[21] Appl. No.: 08/374,402

[22] Filed: Jan. 17, 1995

Related U.S. Application Data

[63] Continuation of application No. 08/135,105, Oct. 12, 1993, abandoned.

[51] Int. Cl.$^6$ .................................................. C07C 51/50
[52] U.S. Cl. ...................... 554/5; 554/6; 554/7; 554/224; 435/411; 800/200; 800/250; 800/DIG. 17
[58] Field of Search .................................. 554/224, 6, 7, 554/5; 435/411; 800/200, DIG. 17, 250

[56] References Cited

U.S. PATENT DOCUMENTS 5,434,283  7/1995  Wang et al. ............................ 554/224

FOREIGN PATENT DOCUMENTS

| 0323753 | 7/1989 | European Pat. Off. |
| 323753 | 7/1989 | European Pat. Off. ......... A01H 1/02 |
| 01965 | 10/1991 | WIPO ............................. C12N 15/00 |
| 05910 | 3/1992 | WIPO ............................... A01H 5/10 |
| 08140 | 4/1993 | WIPO ............................... A01H 5/10 |

OTHER PUBLICATIONS

Pleine et al. Fett. Wiss. Technol., vol. 90, No. 5, pp. 167–171, 1988.
Downey et al., in *Hybridization of Crop Plants*, Fehr et al., eds., pp. 505–509 (1980).
Flick et al., in *Handbook of Plant Cell Culture*, Evans et al., eds., p. 25 (1983).
Harberd, "A simple Effective Embryo Culture Technique for Brassica", *euphytica*, 18:425–429 (1969).
Calhoun et al., "Registration of Indore Rapeseed", *Crop Science*, 23:184–185 (1983).
Pleines et al., Breeding for Improved C18–Fatty Acid Composition in Rapeseed:, *Fett. Wiss. Technol.*, 90(5):167–171 (1988).
Pleines et al., "Genetic control of linoleic acid concentration in seed oil of rapeseed", *Theor. Appl. Genet.*, 78:793–797 (1989).
Pleines et al., Fett. Wiss. Technol., 90(5):167–171, 1988.
Harberd. 1969. Euphytica. 18:425–429.
Calhoun et al. 1983. Crop Science. 23(1): 184–185.
Pleines et al. 1988. Fett. Wiss. Technol. 90(5):167–171.
Pleines et al. 1989. Theor. Appl. Genet. 78: 793–797.
Downey et al. 1980. In Hybridization of Crop Plants. Fehr et al., eds. pp. 505–509.
Flick et al. 1983. In Handbook of Plant Cell Culture. vol. 1 Evans et al., eds. p. 25.

*Primary Examiner*—Deborah D Carr
*Attorney, Agent, or Firm*—Saliwanchik, Lloyd & Saliwanchik

[57] ABSTRACT

A variety of Brassica napus, designated AG019, and varieties essentially derived therefrom, having oil which combines oxidative stability sufficient for industrial applications with a desirable dietary fatty acid profile. Plants, seeds, tissue cultures, and plants regenerated from tissue cultures. Oil having an oleic acid content of from about 71.4% to about 77.4%, a linolenic acid content of no more than about 3%, an oleic:linolenic acid ratio value of at least about 34.0, and an (oleic+linoleic)/linolenic acid ratio value of at least about 41.2. The oil has substantially improved oxidative stability, relatively to normal rapeseed oil, when both are treated with antioxidant.

11 Claims, No Drawings

OIL PRODUCED FROM THE *BRASSICA NAPUS*

This is a continuation of application Ser. No. 08/135,105 filed on Oct. 12, 1993, now abandoned.

FIELD OF THE INVENTION

This invention relates to a variety of *Brassica napus*, and to oil obtained from seed of that variety.

More particularly, the present invention is directed to a variety of *Brassica napus* designated AG019, which produces seed containing about 71–78% oleic acid and no more than about 3% linolenic acid in the seed oil. The oil has improved responsiveness to antioxidants over standard Canola oil, and is useful in food and industrial applications.

DESCRIPTION OF BACKGROUND AND RELEVANT INFORMATION

Over 13% of the world's supply of edible oil in 1985 was produced from the oilseed crop species Brassica, commonly known as rapeseed or mustard. Brassica is the third most important source of edible oil, ranking behind only soybean and palm. Because Brassica is able to germinate and grow at relatively low temperatures, it is also one of the few commercially important edible oilseed crops which can be cultivated in cooler agricultural regions, as well as serving as a winter crop in more temperate zones. Moreover, vegetable oils in general, and rapeseed oil in particular, are gaining increasing consideration for use in industrial applications because they have the potential to provide performance comparable to that of synthetic or mineral/naphthenic-based oils with the very desirable advantage of also being biodegradable.

The performance characteristics, whether dietary or industrial, of a vegetable oil are substantially determined by its fatty acid profile, that is, by the species of fatty acids present in the oil and the relative and absolute amounts of each species. While several relationships between fatty acid profile and performance characteristics are known, many remain uncertain. Notwithstanding, the type and amount of unsaturation present in a vegetable oil have implications for both dietary and industrial applications.

Vegetable oils are subject to oxidative degradation, which can detract from the lubricity and viscosity characteristics of the oil as well as cause changes in color and odor perceived as undesirable. Color and odor are obviously of particular concern in food applications, where the autoxidation of vegetable oils, and the accompanying deterioration of flavor, is referred to as rancidity. The rate of oxidation is affected by several factors, including the presence of oxygen, exposure to light and heat, and the presence of native or added antioxidants and prooxidants in the oil. However, of most pertinence to the present invention, and perhaps generally, is the degree of unsaturation of the fatty acids in the oil.

The fatty acids present in vegetable oils are not equally vulnerable to oxidation. Rather, the susceptibility of individual fatty acids to oxidation is dependent on their degree of unsaturation. Thus, the rate of oxidation of linolenic acid, which possesses three carbon-carbon double bonds, is 25 times that of oleic acid, which has only one double bond, and 2 times that of linoleic acid, which has two. Linoleic and linolenic acids also have the most impact on flavor and odor because they readily form hydroperoxides.

Standard canola oil contains about 8–12% linolenic acid, which places it in a similar category as soybean oil with respect to oxidative, and hence flavor, stability. The oxidative stability of canola oil can be improved in a number of ways, such as by hydrogenating to reduce the amount of unsaturation, adding antioxidants, and blending the oil with an oil or oils having better oxidative stability. For example, blending canola oil with low linolenic acid oils, such as sunflower, reduces the level of 18:3 and thus improves the stability of the oil. However, these treatments necessarily increase the expense of the oil, and can have other complications; for example, hydrogenation tends to increase both the level of saturated fatty acids and the amount of trans unsaturation, both of which are undesirable in dietary applications.

High oleic oils are available, but, in addition to the possible added expense of such premium oils, vegetable oils from crops which have been bred for very high levels of oleic acid can prove unsatisfactory for industrial uses because they retain fairly high levels of polyunsaturated fatty acids, principally linoleic and/or linolenic. Such oils may still be quite usable for dietary applications, including use as cooking oils, but have inadequate oxidative stability under the more rigorous conditions found in industrial applications. Even the addition of antioxidants may not suffice to bring these oils up to the levels of oxidative stability needed for industrial applications; this is probably due to the levels of linolenic acid, with its extremely high susceptibility to oxidation, found in these oils.

As previously stated, oxidative stability is important for industrial applications to extend the life of the lubricant under conditions of heat and pressure and in the presence of chemical by-products. In such applications linolenic acid, and to a lesser extent linoleic acid, are again most responsible for poor oxidative stability.

Therefore, it would be desirable to obtain a variety of *Brassica napus* which is agronomically viable and produces seed oil having a level of oxidative stability sufficient to qualify it for use in dietary applications, and which would additionally be either sufficiently stable alone, or, depending on the precise application, sufficiently responsive to antioxidants, to find use in industrial applications.

European Patent Application EP 323753, to Allelix Inc., is directed to rapeseed oil having an oleic content of at least 79% and not more than 2% erucic acid. A table on page 10 discloses a fatty acid profile of what appears to be a preferred embodiment, constituting a selection designated Topas H6-90-99 with oil having an oleic acid content of 85.84%, a linoleic acid content of 3.54%, and an a-linolenic acid content of 2.68%.

International Application No. PCT/US91/01965, to Pioneer Hi-Bred International, is directed to rapeseed having a saturated fatty acid content of no more than 4% by weight in the form of stearic and palmitic acids, and a post-crushing and extraction erucic acid content of no more than about 2% by weight. As shown by Tables D, G, and H on pages 30, 38, and 39 respectively, the resulting oil also has an oleic acid content of no more than 70.64% by weight, a linoleic acid content of at least 14.24% by weight, and an α-linolenic acid content of at least 8.24% by weight.

International Application No. PCT/US91/05910, to E. I. du Pont, is directed to rapeseed seeds, plants, and oils having altered fatty acid profiles. Several such profiles are described, all of which contemplate a maximum erucic acid content of about 2%, combined with (a) FDA saturates of from about 4.2% to about 5.9% (page 3, lines 18–29), (b) oleic content of from about 69% to about 80% (page 3, line 30-page 4, line 11), (c) linoleic content of about 8.4% to about 14% (page 4, lines 12–23), (d) palmitic acid content of from about 2.7% to about 3.5% (page 4, lines 24–35), (e) palmitic acid content of from about 6% to about 12% (page 4, line 36-page 5, line 17), (f) stearic acid content of from about 0.8% to about 1.1% (page 5, lines 18–27; the reference to palmitic acid at page 5, line 26 would appear to be in error), and (g) linoleic plus linolenic acid content of no more than about 14%, preferably 12.5% (page 5, line 28-page 6, line 2).

International Application No. PCT/US92/08140, to E. I. du Pont, is directed to rapeseed having seed with reduced glucosinolates (and thus reduced sulfur), as well as reduced linolenic acid. The result was a rapeseed having an α-linolenic acid content of about 7% or less (see page 5, lines 5–10), more preferably less than or equal to about 4.1% (page 5, lines 19–23). The lowest content actually obtained appears to have been 1.9%, which was accompanied by relatively low levels of oleic acid (64.1%) and high levels of linoleic acid (25.7%).

SUMMARY OF THE INVENTION

The present invention is directed to a variety of *Brassica napus* designated AG019, as well as to an essentially derived variety of *Brassica napus* which has been essentially derived from AG019. In addition, the present invention is directed to a plant of AG019; a plant of such an essentially derived variety; any plant of the species *Brassica napus* having the physiological and morphological characteristics of AG019; and, to a tissue culture of regenerable cells of any of these plants, as well as to a rape plant regenerated from such a tissue culture.

In another embodiment, the present invention is directed to the seed of AG019, which has been deposited with the American Type Culture Collection (ATCC) under accession number ATCC 75560, and to seed of any of the plants as described in the preceding paragraph.

Also provided by the present invention is oil produced from any of these seeds. The oil has an oleic acid content of from about 71.4% to about 77.4%, and a linolenic acid content of no more than about 3%. Preferably the oleic acid content is from about 72.9% to about 77.0%, and is most preferably from about 72.9% to about 75.3%. The linolenic acid is preferably from about 1.4% to about 2.1%, and most preferably from about 1.7% to about 2.0%.

The oil of the present invention has an oleic:linolenic acid ratio value of from about 34.0 to about 55.3, more preferably from about 36.5 to about 51.3. Moreover, the oil has an (oleic+linoleic)/linolenic acid ratio value of from about 41.2 to about 63.9, and more preferably of from about 44.1 to about 59.6.

The oil may be treated with an effective amount of at least one antioxidant, resulting in substantially improved oxidative stability relative to similarly treated normal rapeseed oil as measured by the ASTM D2272 Rotary Bomb Oxidation Test (RBOT) value. Preferred antioxidants include hindered phenols, such as di-tertiary-butylphenol, and metal deactivators, such as triazole-containing antioxidants, e.g., tolyltriazole or, more generally, the reaction product of tolyltriazole, an aldehyde, and an amine. The hindered phenols and metal deactivators may be used in combination.

DETAILED DESCRIPTION OF THE DRAWING

AG019 is a spring Canola variety which produces an oil with about 71.4–77.4% oleic acid, averaging about 75–75.3%, and no more than about 3% linolenic acid. The following table (Table 1) summarizes the fatty acid composition of AG019 oil along with that from standard Canola.

TABLE 1

| Standard Canola (Western Canada 1992) | | | | | | | | | | |
|---|---|---|---|---|---|---|---|---|---|---|
| Fatty Acid Composition | | | | | | | | | | |
| | 16:0 | 16:1 | 18:0 | 18:1 | 18:2 | 18:3 | 20:0 | 20:1 | 22:0 | 22:1 |
| Canola | 3.7 | 0.3 | 1.7 | 58.4 | 20.9 | 11.1 | 0.6 | 1.6 | 0.3 | 0.6 |

| AG019 Greenhouse Increases (Madison, Wisconsin 1991) | | | | | | | | | |
|---|---|---|---|---|---|---|---|---|---|
| Fatty Acid Composition | | | | | | | | | |
| | 16:0 | 18:0 | 18:1 | 18:2 | 18:3 | 20:0 | 20:1 | 22:0 | 22:1 |
| AG019 | 4.5 | 2.6 | 75.1 | 13.0 | 2.0 | 1.0 | 1.3 | 0.6 | nd |

An average of 200 single plants were analyzed, as 6 seeds bulk/plant; nd = not detected

| AG019 Seed Increase (Argentina 1991–92) | | | | | | | | | | |
|---|---|---|---|---|---|---|---|---|---|---|
| Fatty Acid Composition | | | | | | | | | | |
| | 16:0 | 16:1 | 18:0 | 18:1 | 18:2 | 18:3 | 20:0 | 20:1 | 22:0 | 22:1 |
| AG019 | 3.5 | 0.3 | 1.6 | 74.7 | 16.3 | 1.7 | 0.5 | 1.2 | 0.3 | tr |
| AG019 | 3.3 | 0.4 | 1.7 | 74.2 | 16.2 | 2.1 | 0.5 | 1.2 | 0.3 | tr |
| AG019 | 3.7 | 0.4 | 1.4 | 73.9 | 17.2 | 1.5 | 0.5 | 1.1 | 0.2 | tr |
| Average | 3.5 | 0.4 | 1.6 | 74.2 | 16.6 | 1.8 | 0.5 | 1.2 | 0.3 | tr |

Seeds were bulked from one small lot for analysis; this data represents 3 replicates, of 6 seeds per replicate; tr = trace.

| AG019 Breeder Seed (Deforest, Wisconsin 1992) | | | | | | | | | | | | |
|---|---|---|---|---|---|---|---|---|---|---|---|---|
| Fatty Acid Composition | | | | | | | | | | | | |
| | Bag | GC# | 16:0 | 16:1 | 18:0 | 18:1 | 18:2 | 18:3 | 20:0 | 20:1 | 22:0 | 22:1 |
| AG019 | 1 | 1 | 3.5 | 0.3 | 2.4 | 76.2 | 13.6 | 1.5 | 0.8 | 1.3 | 0.4 | tr |
| AG019 | 2 | 2 | 3.5 | 0.2 | 2.4 | 75.5 | 14.0 | 1.6 | 0.8 | 1.4 | 0.4 | tr |
| AG019 | 3 | 3 | 3.6 | 0.3 | 2.5 | 76.3 | 13.0 | 1.6 | 0.9 | 1.4 | 0.5 | tr |
| AG019 | 4 | 4 | 3.5 | 0.3 | 2.6 | 75.8 | 13.5 | 1.6 | 0.9 | 1.4 | 0.4 | tr |

TABLE 1-continued

| AG019 | 5 | 5 | 3.5 | 0.3 | 2.5 | 76.0 | 13.4 | 1.6 | 0.8 | 1.4 | 0.4 | tr |
| AG019 | 6 | 6 | 3.4 | 0.3 | 2.5 | 75.6 | 13.9 | 1.6 | 0.8 | 1.4 | 0.4 | tr |
| AG019 | 7 | 7 | 3.6 | 0.3 | 2.6 | 75.9 | 13.6 | 1.5 | 0.8 | 1.3 | 0.4 | tr |
| AG019 | 8 | 8 | 3.4 | 0.2 | 2.5 | 76.1 | 13.5 | 1.5 | 0.8 | 1.4 | 0.4 | tr |
| AG019 | 9 | 9 | 3.5 | 0.3 | 2.4 | 76.6 | 13.0 | 1.5 | 0.9 | 1.4 | 0.4 | tr |
| AG019 | 10 | 10 | 3.4 | 0.2 | 2.4 | 75.9 | 14.0 | 1.5 | 0.8 | 1.3 | 0.4 | tr |
| Average | | | 3.5 | 0.3 | 2.5 | 76.0 | 13.6 | 1.6 | 0.8 | 1.4 | 0.4 | tr |

Seeds were harvested from one large field; different lots were harvested into a separate bag each; each bag was then analyzed separately as 6-seed bulk samples.

AG019 Sigco Increase (Breckenridge, Minnesota 1992)

Fatty Acid Composition

| | # | 16:0 | 16:1 | 18:0 | 18:1 | 18:2 | 18:3 | 20:0 | 20:1 | 22:0 | 22:1 |
|---|---|---|---|---|---|---|---|---|---|---|---|
| AG019 | 1 | 3.6 | 0.2 | 2.1 | 74.9 | 14.7 | 1.9 | 0.8 | 1.5 | 0.4 | tr |
| AG019 | 2 | 3.6 | 0.2 | 2.2 | 74.5 | 14.8 | 1.9 | 0.8 | 1.4 | 0.4 | tr |
| AG019 | 3 | 3.6 | 0.2 | 2.3 | 75.3 | 14.2 | 1.8 | 0.8 | 1.4 | 0.4 | tr |
| Average | | 3.6 | 9.2 | 2.2 | 74.9 | 14.6 | 1.9 | 0.8 | 1.4 | 0.4 | tr |

One 25 acre lot was harvested, then analyzed in 3 replicates of 6-seed bulks each.

AG019 Sigco (Breckenridge, Minnesota 1992)

Fatty Acid Composition

| | 16:0 | 16:1 | 18:0 | 18:1 | 18:2 | 18:3 | 20:0 | 20:1 | 22:0 |
|---|---|---|---|---|---|---|---|---|---|
| AG019 Seed | 3.7 | 0.3 | 2.2 | 72.9 | 15.2 | 2.0 | 0.8 | 1.4 | 0.4 |
| Crude Oil | 3.7 | 0.2 | 2.2 | 73.4 | 15.1 | 2.0 | 0.8 | 1.4 | 0.4 |
| RBD Oil | 3.6 | 0.2 | 2.2 | 73.5 | 15.0 | 1.9 | 0.8 | 1.5 | 0.5 |

One 25 acre lot was harvested, yielding approx. 20,000 lbs of seed; 10,000 lbs of seed were sent for processing to POS Pilot Plant Corp. of Saskatoon, Canada AG019 Sigco 2 Acre Foundation Seed Increase (Breckenridge, Minnesota 1993)

Fatty Acid Composition

| Source | 16:0 | 16:1 | 18:0 | 18:1 | 18:2 | 18:3 | 20:0 | 20:1 | 22:0 | 22:1 |
|---|---|---|---|---|---|---|---|---|---|---|
| SG93 S#1 | 3.6 | 0.3 | 2.9 | 76.8 | 12.3 | 1.6 | 0.9 | 1.3 | 0.4 | tr |
| SG93 S#2 | 3.5 | 0.3 | 2.7 | 76.8 | 12.8 | 1.5 | 0.9 | 1.3 | 0.4 | tr |
| SG93 S#3 | 3.5 | 0.3 | 2.8 | 77.4 | 12.1 | 1.4 | 0.9 | 1.3 | 0.4 | tr |
| Average | 3.5 | 0.3 | 2.8 | 77.0 | 12.4 | 1.5 | 0.9 | 1.3 | 0.4 | tr |

One, 2-acre lot was harvested, then analyzed in 3 replicates of 6-seed bulks each.

AG019 Foundation and Certified Production (Minnesota 1993)

Fatty Acid Composition

| Source | 16:0 | 16:1 | 18:0 | 18:1 | 18:2 | 18:3 | 20:0 | 20:1 | 22:0 | 22:1 |
|---|---|---|---|---|---|---|---|---|---|---|
| CD93 #1 | 4.0 | 0.4 | 2.8 | 74.4 | 14.0 | 1.7 | 0.9 | 1.2 | 0.5 | tr |
| CD93 #2 | 4.4 | 0.4 | 3.1 | 71.4 | 15.1 | 2.1 | 1.0 | 1.7 | 0.5 | 0.4 |
| CD93 #3 | 3.9 | 0.3 | 2.8 | 74.4 | 14.5 | 1.6 | 0.9 | 1.2 | 0.4 | tr |
| Average | 4.1 | 0.4 | 2.9 | 73.4 | 14.5 | 1.8 | 0.9 | 1.4 | 0.5 | 0.1 |
| SW93 #1 | 3.8 | 0.3 | 2.7 | 74.3 | 14.6 | 1.8 | 0.8 | 1.2 | 0.4 | tr |
| SW93 #2 | 3.7 | 0.3 | 2.8 | 75.6 | 13.6 | 1.6 | 0.9 | 1.3 | 0.4 | nd |
| SW93 #3 | 3.9 | 0.3 | 2.8 | 73.6 | 15.1 | 1.7 | 0.9 | 1.2 | 0.4 | nd |
| Average | 3.8 | 0.3 | 2.8 | 74.5 | 14.4 | 1.7 | 0.9 | 1.2 | 0.4 | tr |

CD93 = 1993 30 acre Foundation seed production (Minnesota)
SW93 = 1993 85 acre Certified seed production (Minnesota)
For each production, the entire acreage was harvested and analyzed in 3 replicates of 6-seed bulks each. The 0.4% erucic value shown for CD93 #2 is believed to be due to the presence of wild mustard in the harvested field.

For ease of comparison, the information from Table 1 is charted in Table 2, which includes the total monounsaturate content, cumulative linoleic and linolenic content, ratio value of oleic to linolenic acids, and ratio value of combined (oleic+linoleic)/linolenic acids for each example. "Ratio value" means the value obtained by converting a ratio, such as the 75.1:2.0 ratio of oleic:linolenic acids shown for the "Greenhouse '91" entry at the top of Table 2, and converting it to a numerical value, here, 37.6. (With regard to the POS test crush from 1992, Table 2 shows the results of the seed assay only, and not of the subsequent crude and RBD (refined, bleached and deodorized) oil analyses.)

Table 2A provides comparative data among the two parent lines of AG019 (AG013 and BN0010); "Standard Average" canola values, representing the overall fatty acid values for standard canola grown in 28 crop districts in Western Canada (12 in Manitoba, 9 in Saskatchewan, and 7 in Alberta) in 1992, as reported by the Canadian Grain Commission (DeClercq and Daun, *Quality of* 1992 *Western Canadian Canola*, Report to Canola Industry Meeting, Saskatoon, Dec. 1, 1992)(hereinafter "1992 Canadian Grain Commission Report"); and two low linolenic lines, Stellar and Apollo, all as compared with the overall averages for the AG019 data presented in Table 2.

TABLE 2

| Source | Fatty Acid Composition | | | | | | | | | | Total | Total Mono. | 18:2 + 18:3 | 18:1/ 18:3 | (18:1 + 18:2)/ 18:3 |
|---|---|---|---|---|---|---|---|---|---|---|---|---|---|---|---|
| | 16:0 | 16:1 | 18:0 | 18:1 | 18:2 | 18:3 | 20:0 | 20:1 | 22:0 | 22:1 | | | | | |
| *1991–92* | | | | | | | | | | | | | | | |
| Greenhouse '91 | 4.5 | | 2.6 | 75.1 | 13.0 | 2.0 | 1.0 | 1.3 | 0.6 | nd | 100.1 | 76.4 | 15.0 | 37.6 | 44.1 |
| Argentina '91–92 | 3.5 | 0.3 | 1.6 | 74.7 | 16.3 | 1.7 | 0.5 | 1.2 | 0.3 | tr | 100.1 | 76.2 | 18.0 | 43.9 | 53.5 |
| Argentina '91–92 | 3.3 | 0.4 | 1.7 | 74.2 | 16.2 | 2.1 | 0.5 | 1.2 | 0.3 | tr | 99.9 | 75.8 | 18.3 | 35.3 | 43.0 |
| Argentina '91–92 | 3.7 | 0.4 | 1.4 | 73.9 | 17.2 | 1.5 | 0.5 | 1.1 | 0.2 | tr | 99.9 | 75.4 | 18.7 | 49.3 | 60.7 |
| Argentina Average | 3.5 | 0.4 | 1.6 | 74.3 | 16.6 | 1.8 | 0.5 | 1.2 | 0.3 | tr | 100.0 | 75.8 | 18.3 | 42.0 | 51.4 |
| POS Test Crush '92 | 3.7 | 0.3 | 2.2 | 72.9 | 15.2 | 2.0 | 0.8 | 1.4 | 0.4 | | 98.9 | 74.6 | 17.2 | 36.5 | 44.1 |
| Deforest '92 | | | | | | | | | | | | | | | |
| Bag 1/GC# 1 | 3.5 | 0.3 | 2.4 | 76.2 | 13.6 | 1.5 | 0.8 | 1.3 | 0.4 | tr | 100.0 | 77.8 | 15.1 | 50.8 | 59.9 |
| Bag 2/GC# 2 | 3.5 | 0.2 | 2.4 | 75.5 | 14.0 | 1.6 | 0.8 | 1.4 | 0.4 | tr | 99.8 | 77.1 | 15.6 | 47.2 | 55.9 |
| Bag 3/GC# 3 | 3.6 | 0.3 | 2.5 | 76.3 | 13.0 | 1.6 | 0.9 | 1.4 | 0.5 | tr | 100.1 | 78.0 | 14.6 | 47.7 | 55.8 |
| Bag 4/GC# 4 | 3.5 | 0.3 | 2.6 | 75.8 | 13.5 | 1.6 | 0.9 | 1.4 | 0.4 | tr | 100.0 | 77.5 | 15.1 | 47.4 | 55.8 |
| Bag 5/GC# 5 | 3.5 | 0.3 | 2.5 | 76.0 | 13.4 | 1.6 | 0.8 | 1.4 | 0.4 | tr | 99.9 | 77.7 | 15.0 | 47.5 | 55.9 |
| Bag 6/GC# 6 | 3.4 | 0.3 | 2.5 | 75.6 | 13.9 | 1.6 | 0.8 | 1.4 | 0.4 | tr | 99.9 | 77.3 | 15.5 | 47.2 | 55.9 |
| Bag 7/GC# 7 | 3.6 | 0.3 | 2.6 | 75.9 | 13.6 | 1.5 | 0.8 | 1.3 | 0.4 | tr | 100.0 | 77.5 | 15.1 | 50.6 | 59.7 |
| Bag 8/GC# 8 | 3.4 | 0.2 | 2.5 | 76.1 | 13.5 | 1.5 | 0.8 | 1.4 | 0.4 | tr | 99.8 | 77.7 | 15.0 | 50.7 | 59.7 |
| Bag 9/GC# 9 | 3.5 | 0.3 | 2.4 | 76.6 | 13.0 | 1.5 | 0.9 | 1.4 | 0.4 | tr | 100.0 | 78.3 | 14.5 | 51.1 | 59.7 |
| Bag 10/GC# 10 | 3.4 | 0.2 | 2.4 | 75.9 | 14.0 | 1.5 | 0.8 | 1.3 | 0.4 | tr | 99.9 | 77.4 | 15.5 | 50.6 | 59.9 |
| Deforest Average | 3.5 | 0.3 | 2.5 | 76.0 | 13.6 | 1.6 | 0.8 | 1.4 | 0.4 | tr | 99.9 | 77.6 | 15.1 | 49.0 | 57.8 |
| '92 Sigco Increase | 3.6 | 0.2 | 2.1 | 74.9 | 14.7 | 1.9 | 0.8 | 1.5 | 0.4 | tr | 100.1 | 76.6 | 16.6 | 39.4 | 47.2 |
| '92 Sigco Increase | 3.6 | 0.2 | 2.2 | 74.5 | 14.8 | 1.9 | 0.8 | 1.4 | 0.4 | tr | 99.8 | 76.1 | 16.7 | 39.2 | 47.0 |
| '92 Sigco Increase | 3.6 | 0.2 | 2.3 | 75.3 | 14.2 | 1.8 | 0.8 | 1.4 | 0.4 | tr | 100.0 | 76.9 | 16.0 | 41.8 | 49.7 |
| Sigco Average | 3.6 | 0.2 | 2.2 | 74.9 | 14.6 | 1.9 | 0.8 | 1.4 | 0.4 | tr | 100.0 | 76.5 | 16.4 | 40.1 | 47.9 |
| Average for '91–92 | 3.6 | 0.2 | 2.3 | 75.3 | 14.3 | 1.7 | 0.8 | 1.3 | 0.4 | tr | 99.9 | 76.9 | 16.0 | 45.2 | 53.0 |
| *1993* | | | | | | | | | | | | | | | |
| Sigco 2 Acre Foundation Seed Increase - 1993 | | | | | | | | | | | | | | | |
| SG93 S#1 | 3.6 | 0.3 | 2.9 | 76.8 | 12.3 | 1.6 | 0.9 | 1.3 | 0.4 | tr | 100.1 | 78.4 | 13.9 | 48.0 | 55.7 |
| SG93 S#2 | 3.5 | 0.3 | 2.7 | 76.8 | 12.8 | 1.5 | 0.9 | 1.3 | 0.4 | tr | 100.2 | 78.4 | 14.3 | 51.2 | 59.7 |
| SG93 S#3 | 3.5 | 0.3 | 2.8 | 77.4 | 12.1 | 1.4 | 0.9 | 1.3 | 0.4 | tr | 100.1 | 79.0 | 13.5 | 55.3 | 63.9 |
| SG93 Average | 3.5 | 0.3 | 2.8 | 77.0 | 12.4 | 1.5 | 0.9 | 1.3 | 0.4 | tr | 100.1 | 78.6 | 13.9 | 51.3 | 59.6 |
| 1993 Foundation and Certified Production | | | | | | | | | | | | | | | |
| CD93 #1 | 4.0 | 0.4 | 2.8 | 74.4 | 14.0 | 1.7 | 0.9 | 1.2 | 0.5 | tr | 99.9 | 76.0 | 15.7 | 43.8 | 52.0 |
| CD93 #2 | 4.4 | 0.4 | 3.1 | 71.4 | 15.1 | 2.1 | 1.0 | 1.7 | 0.5 | 0.4 | 100.1 | 73.9 | 17.2 | 34.0 | 41.2 |
| CD93 #3 | 3.9 | 0.3 | 2.8 | 74.4 | 14.5 | 1.6 | 0.9 | 1.2 | 0.4 | tr | 100.0 | 75.9 | 16.1 | 46.5 | 55.6 |
| CD93 Average | 4.1 | 0.4 | 2.9 | 73.4 | 14.5 | 1.8 | 0.9 | 1.4 | 0.5 | 0.1 | | 75.3 | 16.3 | 41.4 | 49.6 |
| SW93 #1 | 3.8 | 0.3 | 2.7 | 74.3 | 14.6 | 1.8 | 0.8 | 1.2 | 0.4 | tr | 99.9 | 75.8 | 16.4 | 41.3 | 49.4 |
| SW93 #2 | 3.7 | 0.3 | 2.8 | 75.6 | 13.6 | 1.6 | 0.9 | 1.3 | 0.4 | nd | 100.2 | 77.2 | 15.2 | 47.2 | 55.8 |
| SW93 #3 | 3.9 | 0.3 | 2.8 | 73.6 | 15.1 | 1.7 | 0.9 | 1.2 | 0.4 | nd | 99.9 | 75.1 | 16.8 | 43.3 | 52.2 |
| SW93 Average | 3.8 | 0.3 | 2.8 | 74.5 | 14.4 | 1.7 | 0.9 | 1.2 | 0.4 | tr | | 76.0 | 16.1 | 43.9 | 52.4 |
| Average for '93 | 3.8 | 0.3 | 2.8 | 75.0 | 13.8 | 1.7 | 0.9 | 1.3 | 0.4 | tr | | 76.6 | 15.5 | 45.6 | 53.9 | nd = not detected
tr = trace

TABLE 2A

Comparative Data

| Source | Fatty Acid Composition | | | | | | | | | | Total | Total Mono. | 18:2 + 18:3 | 18:1/ 18:3 | (18:1 + 18:2)/ 18:3 |
|---|---|---|---|---|---|---|---|---|---|---|---|---|---|---|---|
| | 16:0 | 16:1 | 18:0 | 18:1 | 18:2 | 18:3 | 20:0 | 20:1 | 22:0 | 22:1 | | | | | |
| AG013 | 3.2 | | 1.9 | 74.2 | 9.2 | 8.0 | 0.7 | 1.6 | 0.4 | tr | 99.2 | 75.8 | 17.2 | 9.3 | 10.4 |
| BN0010 | 5.2 | | 1.8 | 63.2 | 25.0 | 2.5 | | 0.1 | | 0.1 | 98.8 | 64.3 | 27.5 | 25.3 | 35.3 |

TABLE 2A-continued

Comparative Data

| | Fatty Acid Composition | | | | | | | | | | Total | Total Mono. | 18:2 + 18:3 | 18:1/ 18:3 | (18:1 + 18:2)/ 18:3 |
|---|---|---|---|---|---|---|---|---|---|---|---|---|---|---|---|
| Source | 16:0 | 16:1 | 18:0 | 18:1 | 18:2 | 18:3 | 20:0 | 20:1 | 22:0 | 22:1 | | | | | |
| Standard Average | 3.7 | 0.3 | 1.7 | 58.4 | 20.9 | 11.1 | 0.6 | 1.6 | 0.3 | 0.6 | 99.2 | 60.9 | 32.0 | 5.3 | 7.1 |
| Stellar | 4.1 | | 1.2 | 58.0 | 31.0 | 2.9 | 0.6 | 1.4 | 0.4 | 0.1 | 99.7 | 59.5 | 33.9 | 20.0 | 30.7 |
| Apollo | 4.0 | | 1.9 | 66.0 | 23.5 | 1.9 | 0.7 | 1.3 | 0.4 | 0.1 | 99.8 | 67.4 | 25.4 | 34.7 | 47.1 |
| Overall AG019 Ave. | 3.7 | 0.3 | 2.5 | 75.2 | 14.1 | 1.7 | 0.8 | 1.3 | 0.4 | 0.0 | 100.0 | 76.8 | 15.8 | 45.3 | 53.8 | tr = trace

It should be noted that the inclusion of information herein related to other rapeseed lines, including the AG019 parent lines AG013 and BN0010, for comparative purposes is not an admission that such lines constitute prior art. This information is being included simply to facilitate examination of the present application.

Tables 2 and 2A should be viewed bearing in mind the mechanisms underlying production of fatty acids in vegetable seed oil. The major product of fatty acid synthesis is palmitate (16:0), which is elongated to stearate (18:0). Stearate is then successively desaturated, apparently by a sequence of different enzymes and/or at different cellular locations, to oleate (18:1), linoleate (18:2), and linolenate (18:3).

A comparison of the cumulative levels of 18:0, 18:1, 18:2, and 18:3 in AG019, its parent lines AG013 and BN0010, standard rapeseed, Stellar, Apollo, and the Allelix line from EP 323753, reveals that the cumulative content of these four species of 18-carbon acids (18:0, 18:1, 18:2, and 18:3) varies only within a narrow range, from a low of 92.1% for standard rapeseed to a high of 93.9% for the Allelix variety. From this, it is apparent that the efforts to manipulate oleic, linoleic, and/or linolenic acid content reflected by Allelix EP 323753, Pioneer Hi-Bred PCT/US91/01965, du Pont PCT/US92/08140, and the present invention, represent attempts to alter the normal functioning of desaturase enzymes in rapeseed, i.e., to alter the distribution of 18:0, 18:1, 18:2, and 18:3 within the oil as opposed to significantly affecting the overall amounts of 18-carbon fatty acids present in the oil.

Therefore, selection for very high oleic acid content vegetable oils, such as the Allelix document, presumably focus on selection of plants in which the second desaturation step, of 18:1 to 18:2, is impaired. However, the step in which 18:2 is then desaturated to 18:3 would appear to be, if not independent, at least not directly tied to the 18:1→18:2 desaturation step. This is shown by the fact that while Allelix appears to have identified plants with a substantially impaired 18:1→18:2 desaturation step, yielding an oleic acid content of slightly over 85%, this did not prevent linolenic acid from being present at a level of 2.68% (see table, page 10). In contrast, while AG019 has an overall average oleic acid content of about 75%, its average linolenic acid content is only about 1.7%.

Other distinctions between AG019 and the comparative data are clearly evident, such as in the ratio value of oleic to linolenic acid, shown in the next-to-last column of Table 2A under the heading "18:1/18:3". This ratio is reflective of oxidative stability, which is very responsive to increases in oleic levels and decreases in linolenic levels. The overall average 18:1/18:3 ratio value achieved by AG019 was 45.3, whereas typical ratio values for standard canola range around 5 (see 1992 Canadian Grain Commission Report), and the highest comparative value shown is 34.7, for the low linolenic variety Apollo.

The success of the present invention in obtaining plants wherein the desaturase step leading to linolenic acid is impaired can be most readily quantified by the ratio value of (oleic+linoleic)/linolenic acids, which also provides an additional indicator of oxidative stability. This ratio value is shown in the last column of Table 2A, under the heading "(18:1+18:2)/18:3". While all unsaturates contribute to oxidative degradation, as previously indicated the rate of oxidation of linolenic acid is 25 times that of oleic, and 2 times that of linoleic. Therefore, linolenic acid, which is moreover the only tri-unsaturated fatty acid present in rapeseed in measurable amounts, is a key weak spot in attempts to breed high oxidative stability rapeseed oils.

The present invention achieves remarkable success in minimizing linolenic acid levels, without a concomitant sacrifice in the goals of also obtaining high oleic acid levels and low linoleic acid levels. Thus, while Stellar and Apollo achieve linolenic acid values of 2.9% and 1.9%, respectively, they have oleic acid contents of only 58% for Stellar and 66% for Apollo, compared with the standard average of 58.4% and the AG019 average of 75.2%. Similarly, Stellar shows a linoleic acid content of 31% and Apollo of 23.5%, compared with the standard average of 20.9% and the AG019 average of only 14.1%.

Thus, the closest comparative (oleic+linoleic)/linolenic value appears to come from the Apollo line, with a value of 47.1, compared to the AG019 range of 41.2–63.9 and overall average value of 53.8. Apollo achieved this value at the expense of an above-standard level of linoleic acid (23.5%) and an oleic acid level (66.0%) that is significantly, but not dramatically, higher than standard (58.4%). The contrast between this result and AG019 may be seen by comparing the respective linoleic+linolenic values; 25.4 for Apollo versus 15.8 for AG019, both as compared to 32.0 for standard rapeseed. It is noteworthy that AG019 further contains extremely low levels of erucic acid. In most assays the erucic acid content was below the level of meaningful quantification, i.e., below around 0.05%. The only real exception, which was the 0.4% level measured for the 1993 CD93 #2 sample, is believed to be due to the presence of wild mustard in the field which was commingled with the AG019 during harvesting.

As a result of its unique fatty acid profile, AG019 has substantially improved oxidative stability compared to normal rapeseed, and even compared to parent line AG013. This is shown by the Rancimat data in Table 3; the Rancimat is a relatively low-level, dietary applications-oriented rancidity test, which is conducted at 120° C.:

TABLE 3

| Source | Rancimat Value (@ 120° C.) |
| --- | --- |
| Normal Canola | 1.9 hours |
| AG013 | 3.9 hours |
| AG019 | 6.2 hours |

Unexpectedly, AG019 also has a very substantially improved response to antioxidants, as shown in Table 4:

TABLE 4

| Oil | Antioxidant | RBOT (1) |
| --- | --- | --- |
| Normal rapeseed (2) | None | 13 |
| | 2% hindered phenol (3) | 55 |
| | 2% hindered phenol + 0.05% metal deactivator (4) | 43 |
| AG019 (5) | None | 13 |
| | 2% hindered phenol (3) | 125 |
| | 2% hindered phenol + 0.05% metal deactivator (6) | 150 |

Notes
(1) RBOT = Rotary Bomb Oxidation Test, using ASTM D2272, measured as minutes required for a 25 lb pressure loss.
(2) The normal rapeseed oil used in generating Tables 3 and 4 had the following fatty acid profile:

| 16:0 | 16:1 | 18:0 | 18:1 | 18:2 | 18:3 | 20:0 | 20:1 | 22:0 | 22:1 |
| --- | --- | --- | --- | --- | --- | --- | --- | --- | --- |
| 3.9 | 0.2 | 1.6 | 59.1 | 18.8 | 8.8 | 0.5 | 1.4 | 0.4 | 0.0 |

(3) Di-tertiary-butylphenol.
(4) Reomet ® 39, a triazole derivative (more specifically, a reaction product of tolyltriazole, formaldehyde, and bis-2-ethylhexyl secondary amine) available commerciaily from Ciba-Geigy Corporation.
(5) An RBD (refined, bleached, and deodorized) sample of AG019 was used.
(6) Tolyltriazole.

As may be seen, normal rapeseed oil and AG019 show no detectable difference in baseline stability under the rigorous conditions of the RBOT test. However, when a 2% treat level of hindered phenol is added, normal rapeseed improves to an RBOT value of only 55 minutes whereas AG019 improves to 125 minutes. Even more dramatically, with a combined treat of 2% hindered phenol plus 0.05% metal deactivator, the respective RBOT values declined to 43 minutes for normal rapeseed, but increased to 150 minutes for AG019. (Although different metal deactivators were used, the expected difference in results, if any, attributable to the different performances of these two chemically similar deactivators does not explain the opposite results observed between treatment of normal rapeseed versus treatment of AG019.)

AG019 is best adapted to the spring Canola production area of North Dakota, Minnesota, and western Canada. Yield trials were accordingly conducted in 1992 to compare the agronomic performance of AG019 to that of the elite Canola cultivars Westar, Profit, Delta, and Legend in one location in western Canada. The results of this trial are presented in Table 5.

TABLE 5

| Entry | Yield (1992) kg/ha (% Westar) | Maturity (days) | Height (cm) | Lodging (1–5) | Blackleg (0–9) | Oil (%) |
| --- | --- | --- | --- | --- | --- | --- |
| Westar | 2002 (100) | 101 | 123 | 4.0 | 6.5 | 37.4 |
| Profit | 2182 (109) | 102 | 125 | 3.0 | 3.3 | 38.7 |
| Legend | 2162 (108) | 102 | 126 | 2.3 | 2.3 | 36.9 |
| Delta | 2342 (117) | 104 | 134 | 3.5 | 2.8 | 36.5 |
| AG019 | 2302 (115) | 106 | 133 | 2.8 | 2.5 | 36.5 |

As may be seen, AG019 outyielded Westar by 15%. It is also later in maturity than Westar, has moderate resistance to lodging and to blackleg, and is comparable to Delta in height and oil content.

Additional key characteristics and traits of AG019 are presented in Table 6.

TABLE 6

Objective Description of AG019

SPECIES
*Brassica napus*
TYPE
Spring
PLANT HEIGHT
133 cm tall
same height as Delta
10 cm taller than Westar
Height Class -- Medium tall (Delta)
STEM ANTHOCYANIN
Absent
SEED COTYLEDONS
Max. width fully developed; mean of 50 graded seeds -- Medium
SEEDLING GROWTH HABIT
Leaf rosette -- Upright
LEAVES
Margins (serration) -- weak
Lobing (fully developed leaf on plant or rosette) -- Absent or very weak
Leaf Attachment to Stem -- Partial clasping
Color -- Medium dark green
Glaucosity -- Weak to medium
FLOWERS
Flower Buds Location -- buds at tip of apical meristem
Petal Color -- Yellow
Anther Dotting (at opening of flower) -- 100%
Flowering Class (Spring sown) -- Medium late
PODS (SILIQUE)
Pod Type -- Bilateral single pod
Silique Beak Length -- Medium
Pod Length -- 70 mm
Pod Width -- 5 mm
Pod Habit -- Semi-erect to erect
Pedicel Length -- Long
Ripening Class -- Late
Days to Maturity -- 106 (5 days later than Westar)
SEEDS
3.7 g/1000 unsized seed
Weight same as Westar
Weight Class (grams) -- 3.0–3.9
Seeds Per Pod -- 25
Testa Color -- Black
CHEMICAL COMPOSITION OF SEED
Erucic Acid -- Low (less than 2%)
Glucosinolate Content -- 13 mmoles/g (Low)
Oil Percent -- 36.5%
Protein -- 39.5% (oil free meal)
Fatty Acid Composition -- See Table 1
FROST TOLERANCE
Moderately Susceptible
LODGING RESISTANCE
Moderately Strong
HERBICIDE RESISTANCE
Atrazine -- Susceptible (Jet Neuf)

TABLE 6-continued

Objective Description of AG019

DISEASE RESISTANCE
Sclerotinia Stem Rot (*Sclerotinia sclerotiorum*) -- Susceptible
Blackleg Stem Canker (*Leptosphaeria maculans*) --
Moderate resistance
White Rust (*Albugo candida*) -- High resistance The characteristics described in Table 6, in combination with the fatty acid composition described in Tables 1 and 2, clearly differentiate AG019 from other *Brassica napus* varieties and make it a unique variety.

AG019 can be used for contract production in countries, such as Canada, where spring Canola is adapted. The oil produced from AG019 seed has improved stability compared to standard Canola oil while retaining a desirable dietary fatty acid profile, and thus has applications in both edible and industrial products where these characteristics are required.

It will be readily apparent that, given AG019 as a starting point, the particular benefits afforded by this variety can be manipulated in a number of ways by the skilled practitioner without departing from the scope of the present invention. For example, the seed oil profile present in AG019 can be transferred into other agronomically desirable *Brassica napus* varieties by conventional plant breeding techniques involving cross-pollination and selection of the progeny.

Regeneration techniques may also be used. One initially selects cells capable of regeneration (e.g., seeds, microspores, ovules, pollen, vegetative parts) from a selected plant or variety. These cells may optionally be subjected to mutagenesis, following which a plant is developed from the cells using regeneration, fertilization, and/or growing techniques based on the type of cells mutagenized. Applicable regeneration techniques are known to those in the art; see, for example, Armstrong, C. L., and Green, C. E., *Planta* 164:207–214 (1985); Duncan, D. R. et al., *Planta* 165:322–332 (1985); and, Close, K. R., and Ludeman, L. A., *Plant Science* 52:81–89 (1987), the disclosures of which are hereby incorporated herein in their entireties by reference thereto.

Such manipulations of plants or seeds of AG019, or parts thereof, may lead to the creation of what may be termed "essentially derived" varieties. The International Union for the Protection of New Varieties of Plants (UPOV) has provided the following guideline for determining if a variety has been essentially derived from a protected variety:

[A] variety shall be deemed to be essentially derived from another variety ("the initial variety") when
  (i) it is predominantly derived from the initial variety, or from a variety that is itself predominantly derived from the initial variety, while retaining the expression of the essential characteristics that result from the genotype or combination of genotypes of the initial variety;
  (ii) it is clearly distinguishable from the initial variety; and
  (iii) except for the differences which result from the act of derivation, it conforms to the initial variety in the expression of the essential characteristics that result from the genotype or combination of genotypes of the initial variety.

UPOV, Sixth Meeting with International Organizations, Geneva, Oct. 30, 1992; document prepared by the Office of the Union.

The present invention has of necessity been discussed herein by reference to certain specific methods and materials. The enumeration of these methods and materials was merely illustrative, and in no way constitutes any limitation on the scope of the present invention. It is to be expected that those skilled in the art may discern and practice variations of or alternatives to the specific teachings provided herein, without departing from the scope of the present invention.

What we claim is:

1. Oil from the seed of *Brassica napus*, said oil having an oleic:linolenic aid ratio value of from about 34.0 to about 55.3.

2. The oil as defined by claim 1, wherein said oleic:linoleic acid ratio value is from about 36.5 to about 51.3.

3. The oil as defined by claim 1, further comprising an effective oxidative stabilizing amount of at least one antioxidant, said oil having a substantially improved ASTM D2272 Rotary Bomb Oxidation Test value relative to normal rapeseed oil also treated with said at least one antioxidant.

4. The oil as defined by claim 3, wherein said at least one antioxidant is selected from the group consisting of hindered phenols and metal deactivators.

5. The oil as defined by claim 4, further wherein said at least one antioxidant is di-tertiary-butylphenol.

6. The oil as defined by claim 4, further wherein said metal deactivator is a triazole-containing metal deactivator.

7. The oil as defined by claim 6, wherein said triazole-containing metal deactivator is selected from the group consisting of tolyltriazole and the reaction product of tolyltriazole, an aldehyde, and an amine.

8. The oil as defined by claim 4, further wherein said at least one antioxidant is a combination of di-tertiary-butylphenol and a triazole-containing antioxidant.

9. The oil as defined by claim 1, wherein said oil is produced from seed of a *Brassica napus* variety having all of the physiological and morphological characteristics of the *Brassica napus* variety having ATCC accession number 75560.

10. Oil produced from the seed of *Brassica napus*, said oil hat an (oleic+linoleic)/linolenic acid ratio value of from about 41.2 to about 63.9, and a combined linoeic+liuolenic acid content of no more than about 18.7.

11. The oil as defined by claim 10, wherein said (oleic+linoleic)/linolenic acid ratio value is from about 44.1 to about 59.6.

* * * * *

UNITED STATES PATENT AND TRADEMARK OFFICE
CERTIFICATE OF CORRECTION

PATENT NO. : 5,965,755  
DATED : October 12, 1999  
INVENTOR(S) : John Lawerence Sernyk, et al It is certified that error appears in the above-indentified patent and that said Letters Patent is hereby corrected as shown below:

Column 2, line 40: "a-linolenic" should read --α-linolenic--.

Column 4, line 24: "Drawing" should read --Invention--.

Column 5, line 17: "9.2" should read --0.2--.

Table 2, Source column, line 3: "Argentina '91-92" should read --do.--;

Source column, line 4: "Argentina '91-92" should read --do.--;

Source column, line 20: "'92 Sigco Increase" should read --do.--;

Source column, line 21: "'92 Sigco Increase" should read --do.--.

UNITED STATES PATENT AND TRADEMARK OFFICE
CERTIFICATE OF CORRECTION

PATENT NO. : 5,965,755
DATED : October 12, 1999
INVENTOR(S) : John Lawerence Sernyk, et al Page 2 of 2

It is certified that error appears in the above-indentified patent and that said Letters Patent is hereby corrected as shown below:

Table 2A, column 20:1, row BN0010: "0.1" should read --1.0--.

Column 14, line 21: "aid" should read --acid--;

lines 23-24: "oleic-linoleic" should read --oleic:linolenic--;

line 50: "hat" should read --having--;

line 51: "linoeic + liuolenic" should read --linoleic + linolenic--.

Signed and Sealed this

Twenty-seventh Day of March, 2001

Attest:

NICHOLAS P. GODICI

Attesting Officer

Acting Director of the United States Patent and Trademark Office